US010779962B2

(12) United States Patent
Simonetti et al.

(10) Patent No.: US 10,779,962 B2
(45) Date of Patent: Sep. 22, 2020

(54) SHOWER-SAFE BASE FOOT (71) Applicants: Michael Anthony Simonetti, Imperial Beach, CA (US); Frank Pierce Jones, Chula Vista, CA (US)

(72) Inventors: Michael Anthony Simonetti, Imperial Beach, CA (US); Frank Pierce Jones, Chula Vista, CA (US)

(73) Assignee: Amputech, Imperial Beach, CA (US)

( * ) Notice: Subject to any disclaimer, the term of this patent is extended or adjusted under 35 U.S.C. 154(b) by 0 days.

(21) Appl. No.: 15/443,980

(22) Filed: Feb. 27, 2017

(65) Prior Publication Data
US 2017/0252188 A1    Sep. 7, 2017

Related U.S. Application Data (60) Provisional application No. 62/302,688, filed on Mar. 2, 2016.

(51) Int. Cl.
*A61F 2/66* (2006.01)
*A61F 2/76* (2006.01)
(Continued)

(52) U.S. Cl.
CPC .............. *A61F 2/66* (2013.01); *A61F 2/5044* (2013.01); *A61F 2/60* (2013.01); *A61F 2/76* (2013.01);
(Continued)

(58) Field of Classification Search
CPC .... A61F 2/601; A61F 2/66; A61F 2/76; A61F 3/00; A61F 2002/5089; A61F 2002/6614;
(Continued)

(56) References Cited

U.S. PATENT DOCUMENTS 5,326,352 A * 7/1994 Ferrier ................ A61F 2/60
623/27
5,458,657 A * 10/1995 Rasmusson ............... A61F 2/76
403/362

(Continued)

FOREIGN PATENT DOCUMENTS

JP      06225898 A  *  8/1994  ............... A61F 2/66
WO    WO-91/07150 A1     5/1991

OTHER PUBLICATIONS

International Search Report and Written Opinion issued in International Patent Application No. PCT/US2017/019697, dated Jun. 1, 2017 (dated Jun. 1, 2017).

*Primary Examiner* — Christie L Bahena
(74) *Attorney, Agent, or Firm* — Mintz Levin Cohn Ferris Glovsky and Popeo, P.C.

(57) ABSTRACT

An apparatus includes a detachable foot and a connector for detachably connecting a prosthetic limb socket to the detachable foot. The connector includes a proximal connector detachably connected to the prosthetic limb socket. The proximal connector has a proximal portion of a locking mechanism. There is also a distal connector detachably connected to the detachable foot. The distal connector includes a distal portion of the locking mechanism. The proximal portion of the locking mechanism and the distal portion of the locking mechanism are detachably connecting the proximal connector to the distal connector.

17 Claims, 6 Drawing Sheets (51) Int. Cl.
 *A61F 2/60* (2006.01)
 *A61F 2/50* (2006.01)
(52) U.S. Cl.
 CPC ............ *A61F 2002/5083* (2013.01); *A61F 2002/5089* (2013.01); *A61F 2002/607* (2013.01); *A61F 2002/6614* (2013.01)
(58) Field of Classification Search
 CPC ...... A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692
 See application file for complete search history.

(56) References Cited

U.S. PATENT DOCUMENTS

| | | | |
|---|---|---|---|
| 6,458,163 | B1 | 10/2002 | Slemker et al. |
| 7,303,537 | B1 * | 12/2007 | Snyder ............ A61F 3/00 135/68 |
| 8,778,031 | B1 * | 7/2014 | Latour, Jr. ......... A61H 3/0288 135/65 |
| 2005/0049720 | A1 | 3/2005 | Benson |
| 2005/0109563 | A1 | 5/2005 | Vitale et al. |
| 2005/0288798 | A1 * | 12/2005 | Curtis ............ A61F 2/76 623/38 |
| 2011/0015761 | A1 * | 1/2011 | Celebi ............ A61F 2/76 623/32 |

* cited by examiner

610 — Align the proximal connector and the distal connector such that a locking insert in the proximal connector or the distal connector is aligned with a locking cavity 620 — Insert the locking insert into the locking cavity to align one or more apertures in the locking insert and locking cavity 630 — Insert a pin through the one or more apertures to lock the proximal connector to the distal connector

Fig. 6

SHOWER-SAFE BASE FOOT

RELATED APPLICATION(S)

This application claims the benefit of U.S. Provisional Application No. 62/302,688, filed Mar. 2, 2016, titled "Shower-Safe Base Foot," which is hereby incorporated by reference in its entirety.

TECHNICAL FIELD

The subject matter described herein relates to systems and methods for interchangeably connecting prosthetic limbs.

BACKGROUND

Prosthetic limbs can interface with attachments to allow a person to perform activities similarly to those without prosthetic limbs. In the case of prosthetic legs or feet, attachments to the prosthetic limbs can include features allowing walking, standing, running, or the like.

SUMMARY

In a first aspect, an apparatus includes a detachable foot and a connector for detachably connecting a prosthetic limb socket to the detachable foot. The connector includes a proximal connector detachably connected to the prosthetic limb socket. The proximal connector has a proximal portion of a locking mechanism. There is also a distal connector detachably connected to the detachable foot. The distal connector includes a distal portion of the locking mechanism. The proximal portion of the locking mechanism and the distal portion of the locking mechanism are detachably connecting the proximal connector to the distal connector.

In some variations, the locking mechanism can include a locking insert longitudinally extending from one of the proximal connector or the distal connector, a locking cavity formed in the other of the proximal connector or the distal connector and shaped to receive the locking insert, a locking element that reversibly locks the locking insert into the locking cavity.

The locking insert can further include a locking insert aperture laterally extending through the locking insert and shaped to receive the locking element, the locking cavity formed by a longitudinally extending wall. The longitudinally extending wall can include a locking cavity aperture laterally extending through the longitudinally extending wall and shaped to receive the locking element. The locking element can be a pin extending through the locking insert aperture and the locking cavity aperture to prevent longitudinal separation of the proximal connector and the distal connector.

The locking insert and the locking cavity can have a rectangular cross-section.

The proximal connector can further include a top portion conically shaped to narrow a bottom diameter of a bottom end of the proximal connector to a top diameter of a top end of the proximal connector.

The proximal connector can further include a top cavity formed by a top wall. The top cavity can be shaped to receive a socket insert. The top wall can include a top aperture extending laterally through the top wall to intersect the socket insert.

The top aperture can be threaded to accept a set screw locking the proximal connector to the socket insert.

The distal connector can further include a bottom insert shaped to extend into a detachable foot cavity in the detachable foot and shaped to allow locking of the detachable foot to the distal connector.

A shape of the bottom insert can be pyramidal and a side surface of the bottom insert can be angled to resist removal of the bottom insert from the detachable foot cavity when a set screw is inserted through the detachable foot to abut the side surface.

The apparatus can also include a separating plate between the bottom insert and the locking insert, the separating plate extending laterally from the locking insert.

The detachable foot can be a shower-safe foot comprising a base plate extending laterally from a pylon connected to the prosthetic limb socket. The base plate can include legs extending longitudinally from the base plate. The pylon can be connected to the connector positioned between the pylon and the prosthetic limb socket.

A central leg can extend longitudinally from the base plate and centered along a central axis of the pylon.

A least one of the legs and the central leg can terminate in a rubber foot shaped to fit over a distal portion of the at least one of the legs or the central leg.

The base plate can be planar and include a lateral extension having a distal end connected to at least one of the legs.

The pylon can connect to the base plate at a connection point on the base plate and the connection point can be off-center from a center of the base plate.

In an interrelated aspect, a method for connecting a connector for detachably connecting a prosthetic limb socket to a detachable foot includes aligning the proximal connector and the distal connector such that a locking insert in the proximal connector or the distal connector is aligned with a locking cavity. The locking insert is inserted into the locking cavity to align one or more apertures in the locking insert and locking cavity. A pin is inserted through the one or more apertures to lock the proximal connector to the distal connector.

The connector in the method includes a proximal connector detachably connected to the prosthetic limb socket, the proximal connector including a proximal portion of a locking mechanism. The connector also includes a distal connector detachably connected to the detachable foot, the distal connector including a distal portion of the locking mechanism. The proximal portion of the locking mechanism and the distal portion of the locking mechanism detachably connecting the proximal connector to the distal connector.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to particular implementations, it should be readily understood that such features are not intended to be limiting. The claims that follow this disclosure are intended to define the scope of the protected subject matter.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

In many instances it can be advantageous for a user to be able to replace one type of prosthetic limb for another. For example, when walking or for everyday use, one type of prosthetic limb can be a prosthetic foot. A prosthetic foot can have a shoe or other similar adornment. Other types of prosthetic feet can be used when special circumstances merit. For example, in a bathtub or shower, a specialized prosthetic foot could be used that is resistant to water and also has improved traction on a slippery surface. In some situations, changing from one type of prosthetic foot to another can occur in situations that are less safe or otherwise not ideal. Also, some users may have additional disabilities or physical limitations which can make interchanging prosthetic limbs even more challenging. To address this problem, among others, the instant application provides systems and methods for providing a quick-release connector that allows fast and simple interchanging of prosthetic limbs.

Figure 1:
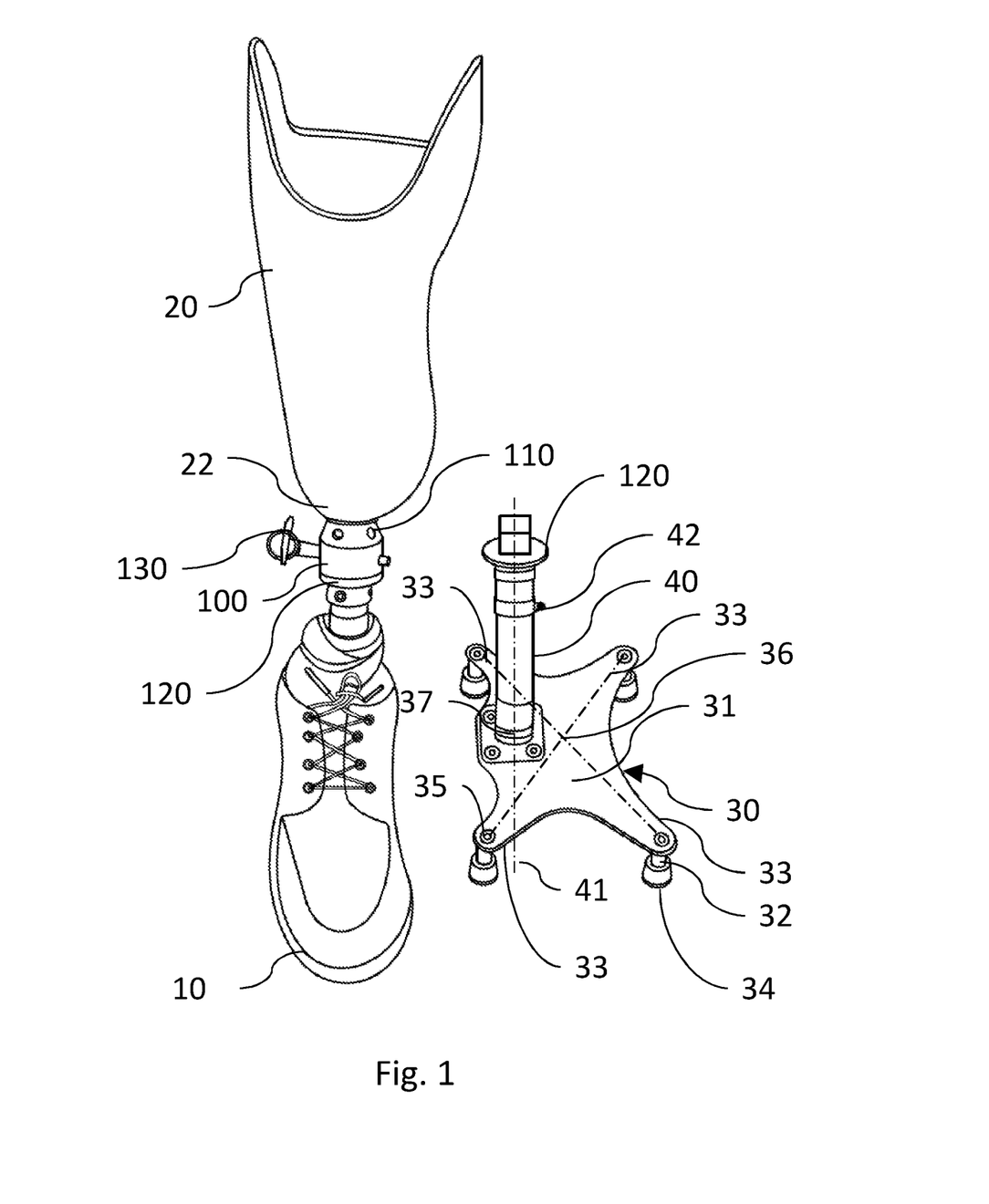
FIG. 1 is a diagram illustrating a simplified perspective view of an exemplary first detachable foot attached to a prosthetic limb socket by a connector in accordance with certain aspects of the present disclosure.
Figure 2:
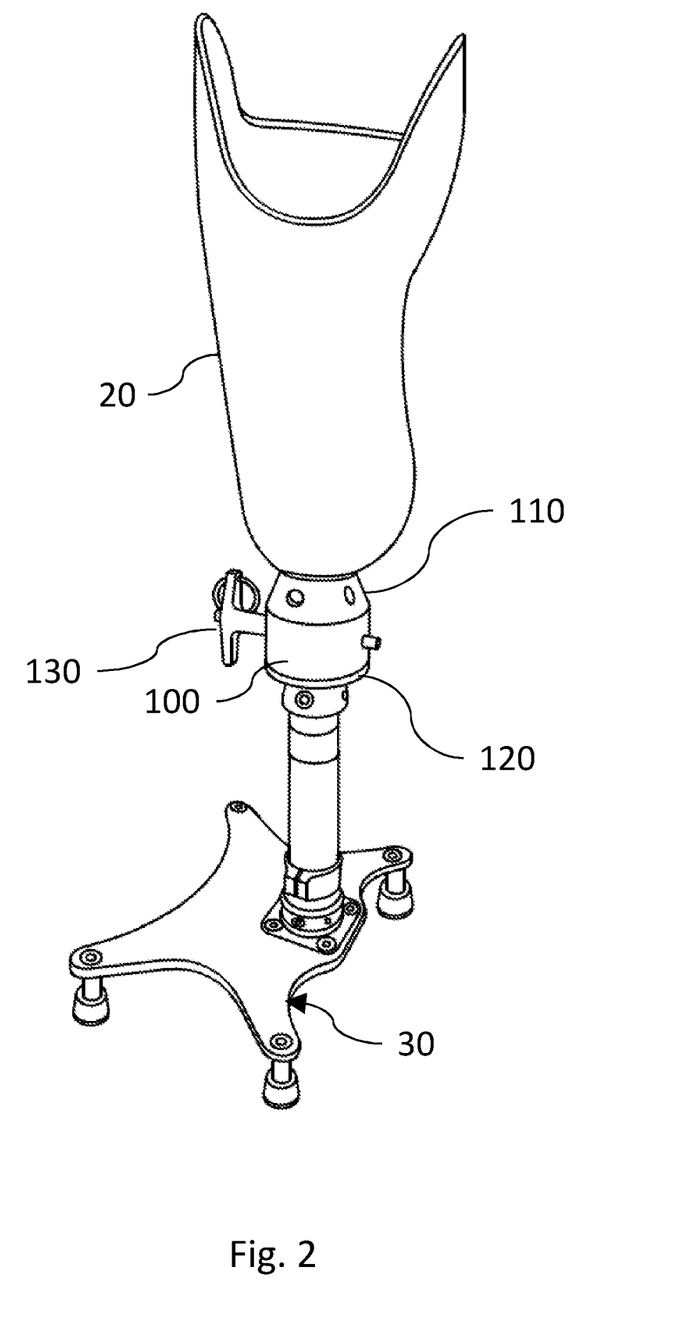
FIG. 2 is a diagram illustrating a simplified perspective view of an exemplary second detachable foot attached to a prosthetic limb socket by a connector in accordance with certain aspects of the present disclosure.

FIG. 1 is a diagram illustrating a simplified perspective view of an exemplary first detachable foot 10 connected to a prosthetic limb socket 20 by a connector 100 in accordance with certain aspects of the present disclosure. FIG. 2 is a diagram illustrating a simplified perspective view of an exemplary second detachable foot connected to a prosthetic limb socket 20 by a connector 100 in accordance with certain aspects of the present disclosure.

The limb of the user can be secured inside the prosthetic limb socket 20. The connector 100 can detachably connect a prosthetic limb socket 20 to a detachable foot 10. In FIG. 1 the detachable foot 10 shown connected to the limb socket 20 can be, for example, a foot used for working or walking. Another type of detachable foot, a shower-safe foot 30, is shown next to the work foot.

A pylon 40 can extend longitudinally from the base of the shower-safe foot 30 or the detachable foot 10. The pylon 40 can be an adjustable or custom fit length of material that connects the base to the connector 100. The length of the pylon 40, also referred to herein as the deck height, limits the adjustment of the overall length of the prosthetic limb. Among other things, the subject matter described herein has the advantage of maximizing the available deck height in order to allow the widest range of lengths of detachable feet to be used. This is accomplished, in part, by the compact nature of the connector 100.

The connector 100 can connect the proximal end 42 of the pylon 40 to the distal end 22 of the prosthetic limb socket 20. To allow for the exchange of different types of prosthetic feet, the connector 100 can separate into two portions. A proximal portion, referred to herein as a proximal connector 110, can remain attached to the prosthetic limb socket 20. Similarly, a distal portion, referred to herein as a distal connector 120, can remain attached to the detachable foot 10. The two portions of the connector 100 can be detachably connected by means of a locking element 130. As shown in FIG. 1, the locking element 130 can be, for example, a pin that holds the two portions together. A user can take the pin out to replace one prosthetic foot with another. The new prosthetic foot can be locked into place by the locking element 130 (e.g. the reinsertion of the pin). One example of the new prosthetic foot locked into place by the locking element 130 is shown in FIG. 2. Here, the shower-safe foot 30 is locked to the prosthetic limb socket 20 by the connector 100.

The shower-safe foot 30 can provide additional stability and/or traction to a user in a slippery environment such as a shower or bath tub. The shower-safe foot 30 can include a base plate extending laterally from the pylon 40 connected to the prosthetic limb socket 20. The base plate 31 can have any number of legs 32 that extend longitudinally from the base plate 31 of the shower-safe foot 30 (e.g., at least three legs, at least four legs, at least five legs, or the like). As shown in FIGS. 1 and 2, the legs 32 extend downward (again in the longitudinal direction) to provide a stable footing for the shower-safe foot 30 and can have a grooved bottom. In some implementations, there can be a central leg that can extend longitudinally from the base plate 31 and centered along a central axis 41 of the pylon 40. By positioning the central leg along the central axis 41 of the pylon 41, the central leg can be in along a direct line of force applied by the limb of the user.

In some implementations, the legs 32 and/or central leg of the shower-safe foot 30 can terminate in a cap 34 that can provide increased traction on a slippery surface. The caps 34 can be plastic or rubber and shaped to fit over a distal portion of the legs 32 and/or central leg.

The base plate 31 can be planar and include one or more lateral extensions 33. The lateral extensions 33 can generally extend the lateral dimension of the base plate 31 while minimizing the required material and/or weight needed to provide a stable support for the user. As shown in FIGS. 1 and 2, the lateral extensions 33 can be elongate and form a contiguous piece with the base plate 31. The particular design of the lateral extensions 33 can vary, for example, they can be straight, curved, or the like. The lateral extensions 33 can each have a distal end 35 connected to a leg 32. Similarly, in other implementations, the lateral extensions 33 can smoothly transition into the legs as opposed to being a separate piece connected by a fastener, as shown.

The pylon 40 can connect to the base plate 31 at any point on the surface of the base plate 31. In some implementations, such as those illustrated in FIGS. 1 and 2, the pylon 40 can connect to the base plate 31 at a connection point 37 that is off-center from a center 36 of the base plate 31. The center 36 can be defined, for example, as the intersection of lines between four of the legs 32. It is contemplated that, more generally, the center 36 of the base plate 31 can be a point that is proximate to a center of mass of the base plate 31 or otherwise a point generally in an interior region of the base plate 31 such that the overall shape of the base plate 31 is symmetrical about it, or nearly so. For implementations where the connection point 37 is off-center, this can provide additional stability by making it more difficult for a user to tip when standing. Also, in these implementations, the majority of the base plate 31 can be positioned to one side of the user, for example an outer side, such that there can be more clearance between the shower-safe foot 30 and the other foot of the user.

In some implementations, the proximal connector 110, the lateral connector 120, or both can be constructed from, for example, aluminum, steel, stainless steel, copper, titanium, plastic, or any combination thereof.

As used herein, the term "proximal" generally refers to a location generally closer to a body of a user than a location further from a body of user, referred to herein as "distal." For example, the proximal portion of the connector 100 can be the portion that is closest to the prosthetic limb socket 20, and hence a body of the user. Similarly, the distal portion of the connector 100 can be the portion connected to the detachable foot 10, and hence further from the body of the user.

Also, as used herein, the term "longitudinal" refers to a generally lengthwise direction along the prosthetic limb. The direction need not be strictly linear and can include any number of angles, terms, twists, or other variations and path that can be implemented in a prosthetic limb. Similarly, the term "lateral" refers to a direction generally transverse to the longitudinal direction.

While some implementations of the current subject matter are described in reference to a prosthetic leg, other types of prosthetic appendages or appliances can be used with the connector 100. Other implementations can include prosthetic arms, hands, fingers, or any other sort of prosthetic attachment, artificial limb, tool, or the like. For example, the connector 100 described herein could allow the connection of different types of prosthetic hands to a user. Similarly, although the features described herein are often used with a prosthetic limb socket 20, the connection can be considered to interface with any sort of prosthetic limb attachment designed to allow the attachment of a variety of prosthetic limbs.

The proximal connector 110 can be portion of the connector 100 that is closest to the user. Similarly, the distal connector 120 can be a portion of the connector 100 that is furthest from the user. The proximal connector 110 and the distal connector 120 can be connected and locked with a locking mechanism. As described in greater detail below, the proximal portion of the locking mechanism and the distal portion of the locking mechanism can detachably connect the proximal connector 110 to the distal connector 120.

Figure 3:
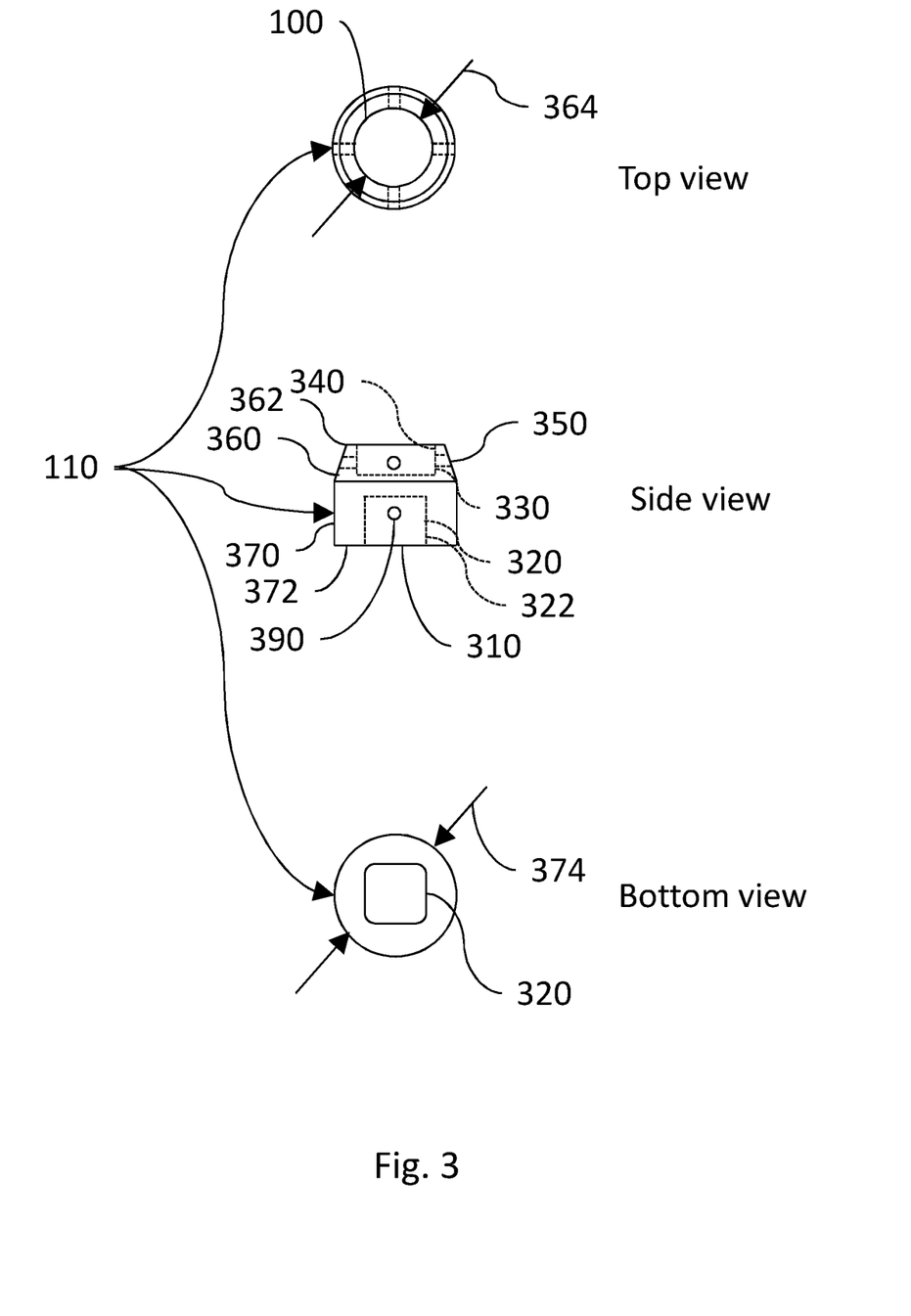
FIG. 3 is a simplified diagram of an exemplary proximal connector in accordance with certain aspects of the present disclosure.
Figure 4:
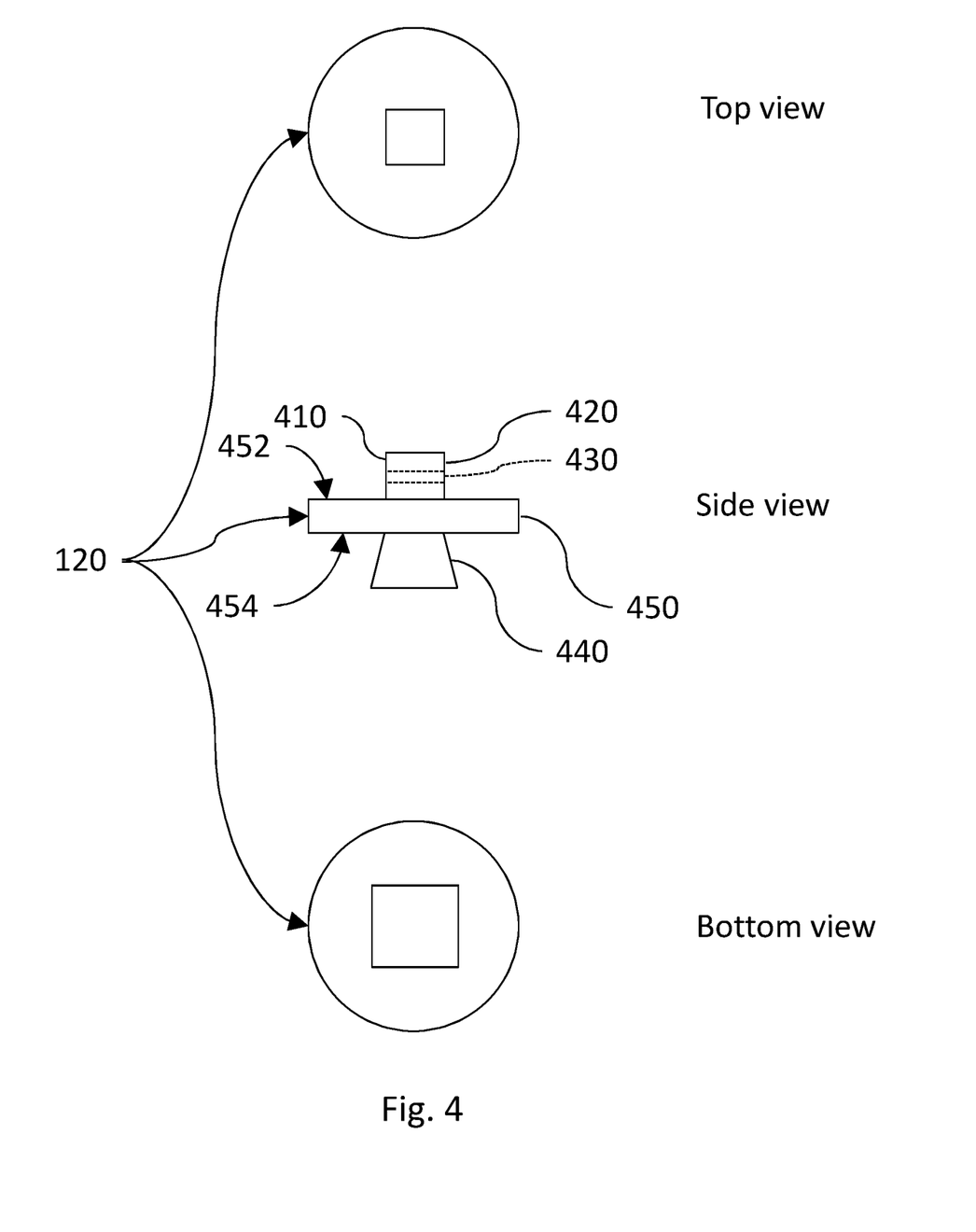
FIG. 4 is a simplified diagram of an exemplary distal connector in accordance with certain aspects of the present disclosure.

FIG. 3 is a simplified diagram of an exemplary proximal connector 110 in accordance with certain aspects of the present disclosure. FIGS. 3 and 4 show two halves of the connector 100; a proximal connector 110 (FIG. 3) and a distal connector 120 (FIG. 4). The proximal connector 110 can be detachably connected to the prosthetic limb socket 20 (shown in FIG. 2) and can further include a proximal portion 310 of a locking mechanism. In the example of FIG. 3, the proximal portion 310 of the locking mechanism can include a locking cavity 320 shaped to receive a locking insert (shown in FIG. 4). The locking cavity 320 can be formed in the bottom portion 370 of the proximal connector 110. The locking cavity 320 can be formed by a longitudinally extending wall 322. There can also be one or more locking cavity apertures 390 extending laterally through the longitudinally extending wall 322. There can be any number of locking cavity apertures 390 for securing the proximal connector 110 to the distal connector 120. In some implementations, there can be one, two, three, four, six, or eight, locking cavity apertures 390. The locking cavity apertures 390 can be symmetrically positioned along a diameter of the proximal connector 110.

The proximal connector 110 can also include a top portion 360 configured to connect to the prosthetic limb socket 20. In some implementations, the top portion 360 of the proximal connector 110 can include a top cavity 330 formed by a top wall 340. The top cavity 330 can be shaped to receive a socket insert. The socket insert can extend from the prosthetic limb socket 20 to insert into the top cavity 330. The top wall 340 can include a top aperture 350 extending laterally through the top wall 340 to intersect the socket insert. In some implementations, the top aperture 350 can be threaded to accept a set screw locking the proximal connector 110 to the socket insert. There can be any number of top apertures 350 for securing the proximal connector 110 to the socket insert. In some implementations, there can be one, two, three, four, six, or eight, top apertures 350. The top apertures 350 can be symmetrically positioned along a diameter of the proximal connector 110.

In some implementations, the top portion 360 can be conically shaped to narrow a bottom diameter 374 of a bottom end 372 of the proximal connector 110 to a top diameter 364 of a top end 362 of the proximal connector 110.

FIG. 4 is a simplified diagram of a distal connector 120 in accordance with certain aspects of the present disclosure. A distal connector 120 can be detachably connected to the detachable foot 10. In some implementations, any number of detachable feet can each have a distal connector 120 to allow connection between the connector 100 and detachable foot. The distal connector 120 can remain connected to the detachable foot. In this way, different kinds of detachable feet can be connected to the proximal connector 110.

The distal connector 120 can include a distal portion 410 of the locking mechanism. As shown in FIG. 4, the distal portion 410 of the locking mechanism can be a locking insert 420 that interfaces with the proximal portion 110 of the locking mechanism (shown in FIG. 3). There can be a locking insert aperture 430 extending through the locking insert 420 to allow engagement of the locking element 130. Further details locking mechanism are described with reference to FIG. 5.

Some implementations of the current subject matter illustrate the locking insert 420 extending from one half of the connector 100 into a locking cavity 320 of the other half of the connector 100. In particular, the implementations illustrated in FIG. 3 and FIG. 4 show the proximal connector 110 having a cavity and the distal connector 120 having an insert shaped to interface with the cavity. However, in general, the cavity can be in either (or both) of the halves of the connector 100. Similarly, the insert shaped to interface with the cavity can be on either (or both) of the halves of the connector 100. In particular, in some implementations, the insert/cavity configuration shown in FIG. 3 and FIG. 4 can be reversed. In other implementations, there can be multiple cavities and inserts in each half of the connector 100. For each cavity and insert pair, there can be a corresponding locking element 130 to lock the insert(s) into the cavity/cavities. In other implementations, a locking element 130 is not required (e.g. where the insert and cavity act as a guide to align the two halves of the connector 100) in a lateral position or angular configuration.

The distal connector 120 can also include a bottom insert 440 shaped to extend into a detachable foot cavity in the detachable foot 10. The bottom insert 440 can be shaped to allow locking of the detachable foot 10 to the distal connector 120. In some implementations, a shape of the bottom insert 440 can be pyramidal. The pyramidal shape can include a side surface of the bottom insert 440 that can be angled to resist removal of the bottom insert 440 from the detachable foot cavity. The bottom insert 440 can be secured in the detachable foot cavity, for example, when a set screw is inserted through the detachable foot 10 to abut the side surface.

In other implementations, the distal connector 120 can include a separating plate 450 between the bottom insert 440 and the locking insert 420. The separating plate 450 can laterally extend from the locking insert 420. As shown in FIG. 4, the separating plate 450 can include a top surface 452 that can provide a physical stop for an abutting proximal connector 110. The separating plate 450 can also include a bottom surface 454 that can provide a physical stop for an abutting pylon 40. In some implementations, the separating plate 450 can be cylindrically shaped to have the same diameter as the bottom diameter 374 of the proximal connector 110 and provide a flush outer surface when locked to the proximal connector 110.

Figure 5:
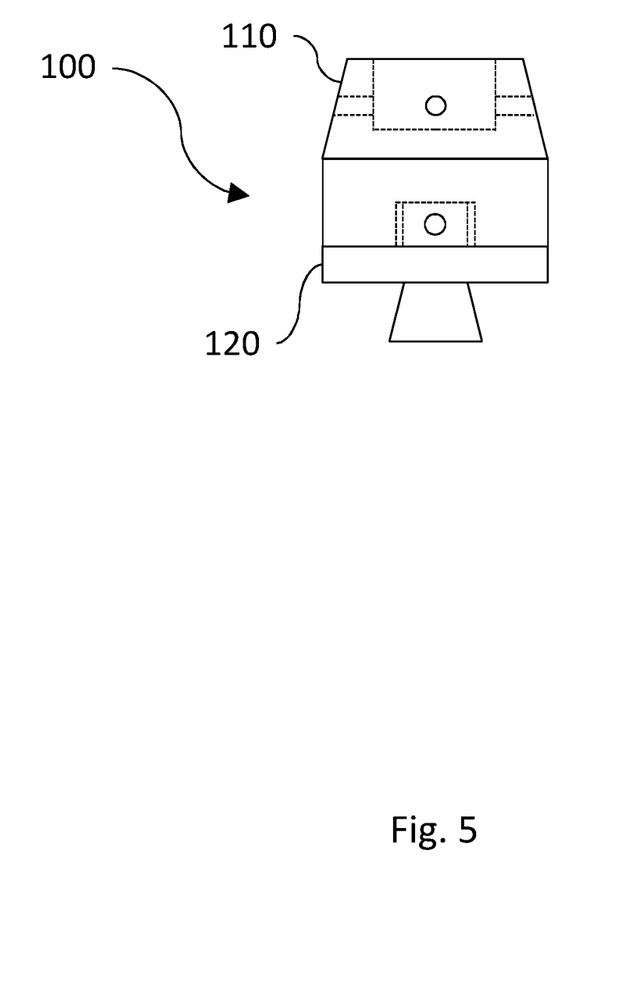
FIG. 5 is a simplified diagram of the proximal connector abutting the distal connector in accordance with certain aspects of the present disclosure.

FIG. 5 is a diagram illustrating a simplified diagram of the proximal connector 110 abutting the distal connector 120 in accordance with certain aspects of the present disclosure. As described herein, some implementations of the current subject matter can include a locking mechanism to allow different detachable feet to be connected to a user and locked into place. In these implementations, one part of the connector 100 can be attached to the prosthetic limb socket 20 and the other part of the connector 100 can be attached to the detachable foot 10. As shown in FIG. 5, the proximal connector 110 and the distal connector 120 can be mated to form the connector 100. Once together, for example in an abutting configuration, a locking mechanism can be engaged to lock the proximal connector 110 to the distal connector 120 together. In this way, the proximal portion of the locking mechanism and the distal portion of the locking mechanism can detachably connect the proximal connector 110 to the distal connector 120.

In some implementations, the proximal connector 110 can remain permanently or semi-permanently (e.g. fixed with set screws) attached to the prosthetic limb socket 20. Similarly, the distal connector 120 can remain permanently or semi-permanently (e.g. fixed with set screws) attached to the detachable foot 30. In this way, the primary attachment/detachment means for exchanging different types of detachable feet 30 is through operation of the connector 100.

There can be any number of means for removably connecting (and/or locking) the proximal connector 110 and the distal connector 120. One example, described in further detail below, can utilize a combination of inserts (in one half of the connector 100) and cavities (in the other half of the connector 100) such that an insert can be locked into a cavity by a pin or other locking element 130.

In some implementations, the locking insert 420 can longitudinally extend from one of the proximal connector 110 or the distal connector 120. The locking insert 420 can be shaped to fit into the locking cavity 320. In the example of FIGS. 4 and 5, the locking insert 420 is a cubic or rectangular cubic feature. The shape and physical dimensions of the locking insert 420 and the locking cavity 320 can vary as desired by one skilled in the art. For example, the locking insert 420 and the locking cavity 320 can be cylindrically shaped, rectangular shaped, cubic, elongated, or the like. Similarly, the cross-sectional shape of the locking insert 420 and/or the locking cavity 320 can be circular, square, rectangular, elliptical, or the like.

The locking insert 420 can further include a locking insert aperture 430 laterally extending through the locking insert 420 and shaped to receive the locking element 130. For example, when the locking element 130 is a pin with a round cross-section, the locking insert aperture 430 can also be round and of a slightly larger diameter than the pin.

A locking cavity 320 can be formed in the other of the proximal connector 110 or the distal connector 120 and shaped to receive the locking insert 420. In particular, the locking cavity 320 can be formed by a longitudinally extending wall of the distal connector 120. The longitudinally extending wall 322 can include a locking cavity aperture 390 laterally extending through the longitudinally extending wall 322 and shaped to receive the locking element 130. The locking cavity aperture 390 can be shaped similarly to the locking insert aperture 430. As shown in FIG. 5, when the locking element 130 is a pin, the pin can be inserted through the locking cavity aperture 390 and into the locking insert aperture 430 to lock the distal connector 120 to the proximal connector 110.

As described herein, there can be any number of means for detachably locking the proximal connector 110 to the distal connector 120. In some implementations, for example those shown in FIGS. 1-4, the locking element 130 can be a pin inserted through aligned apertures in the proximal connector 110 and the distal connector 120. In this way, the locking element 130 reversibly locks the locking insert into the locking cavity. The locking element 130 can extend through the locking insert aperture 350 and the locking cavity aperture 390 to prevent longitudinal separation of the proximal connector 110 and the distal connector 120.

Although shown herein with a single locking element 130 (e.g. pin), any number of locking elements 130, and corresponding apertures in the connector 100, can be implemented. Also, other means for locking the proximal connector 110 to the distal connector 120 can be used. For example, instead of a pin, the locking element 130 can be a screw, latch, pin with spring-loaded features that extend laterally from the body of the pin to resist withdrawal of the pin from the aperture, or the like.

Figure 6:
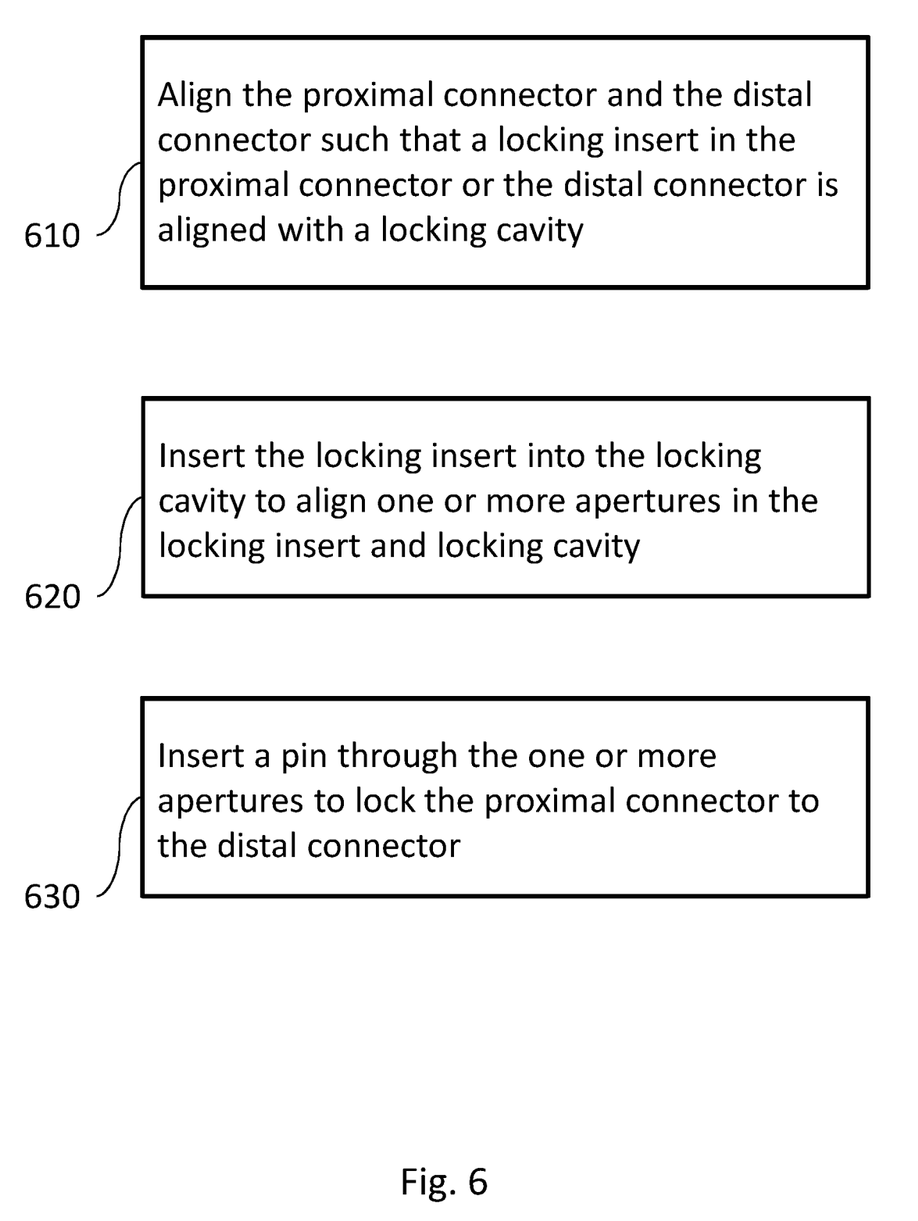
FIG. 6 is a simplified diagram for an exemplary method of locking the detachable foot to the prosthetic limb socket with the connector in accordance with certain aspects of the present disclosure.

FIG. 6 is a simplified diagram for an exemplary method of locking the detachable foot 10 to the prosthetic limb socket 20 with the connector 100 in accordance with certain aspects of the present disclosure.

One of the advantages of the subject matter described herein is the ability to quickly and easily exchange different types of detachable feet or other prosthetic limbs or attachments using the connector 100. As described herein, with reference to the prosthetic feet, one method of use of the connector 100 is described below.

At 610, the proximal connector 110 and the distal connector 120 can be aligned such that a locking insert 420 in the proximal connector 110 or the distal connector 120 is aligned with a locking cavity 320.

At 620, the locking insert 420 can be inserted into the locking cavity 320 to align one or more apertures in the locking insert 420 and locking cavity 320.

At 630, a pin can be inserted through the one or more apertures to lock the proximal connector 110 to the distal connector 120.

Similarly, another method can include reversing the above steps to unlock and separate the proximal connector 110 from the distal connector 120.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, computer programs and/or articles depending on the desired configuration. Any methods or the logic flows depicted in the accompanying figures and/or described herein do not necessarily require the particular order shown, or sequential order, to achieve desirable results. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. The implementations described above can be directed to various combinations and subcombinations of the disclosed features and/or combinations and subcombinations of further features noted above. Furthermore, above described advantages are not intended to limit the application of any issued claims to processes and structures accomplishing any or all of the advantages.

Additionally, section headings shall not limit or characterize the invention(s) set out in any claims that may issue from this disclosure. Specifically, and by way of example, although the headings refer to a "Technical Field," such claims should not be limited by the language chosen under this heading to describe the so-called technical field. Further, the description of a technology in the "Background" is not to be construed as an admission that technology is prior art to any invention(s) in this disclosure. Neither is the "Summary" to be considered as a characterization of the invention(s) set forth in issued claims. Furthermore, any reference to this disclosure in general or use of the word "invention" in the singular is not intended to imply any limitation on the scope of the claims set forth below. Multiple inventions may be set forth according to the limitations of the multiple claims issuing from this disclosure, and such claims accordingly define the invention(s), and their equivalents, that are protected thereby.

What is claimed is:

1. An apparatus comprising:
   a detachable foot, the detachable foot being a shower-safe foot comprising:
      a base plate extending laterally from a pylon connected to a prosthetic limb socket,
      the base plate comprising a plurality of legs extending longitudinally form the base plate,
      the plurality of legs comprising a central leg extending longitudinally from the base plate and centered along a central axis of the pylon, the central axis of the pylon at a fixed perpendicular angle to the base plate, the central leg aligned with the pylon, at least one of the plurality of legs having a grooved bottom; and
   a connector for detachably connecting the prosthetic limb socket to the detachable foot, the connector comprising:
      a proximal connector detachably connected to the prosthetic limb socket, the proximal connector comprising a proximal portion of a locking mechanism; and
      a distal connector detachably connected to the detachable foot, the distal connector comprising a distal portion of the locking mechanism, the proximal portion of the locking mechanism and the distal portion of the locking mechanism detachably connecting the proximal connector to the distal connector,
      the locking mechanism comprising:
         a locking insert longitudinally extending from one of the proximal connector or the distal connector;
         a locking cavity formed in the other of the proximal connector or the distal connector and shaped to receive the locking insert; and
         a locking element that reversibly locks the locking insert into the locking cavity, the locking element performing the locking while being external to and below the prosthetic limb socket;
         the locking insert further comprising a locking insert aperture laterally extending through the locking insert and shaped to receive the locking element;
         the locking cavity formed by a longitudinally extending wall, the longitudinally extending wall comprising a locking cavity aperture laterally extending through the longitudinally extending wall and shaped to receive the locking element;
         the locking element comprising a spring-loaded pin extending through the locking insert aperture and the locking cavity aperture to prevent longitudinal separation of the proximal connector and the distal connector, the locking element engaging with the locking insert aperture and the locking cavity without threads.

2. The apparatus of claim 1, wherein the locking insert and the locking cavity have a rectangular cross-section.

3. The apparatus of claim 1, the proximal connector further comprising a top portion conically shaped to narrow a bottom diameter of a bottom end of the proximal connector to a top diameter of a top end of the proximal connector.

4. The apparatus of claim 1, the proximal connector further comprising a top cavity formed by a top wall, the top cavity shaped to receive a socket insert, the top wall comprising a top aperture extending laterally through the top wall to intersect the socket insert.

5. The apparatus of claim 4, wherein the top aperture is threaded to accept a set screw locking the proximal connector to the socket insert.

6. The apparatus of claim 1, the distal connector further comprising a bottom insert that extends into a detachable foot cavity in the detachable foot and allows locking of the detachable foot to the distal connector.

7. The apparatus of claim 6, wherein a shape of the bottom insert is pyramidal and wherein a side surface of the bottom insert is angled to resist removal of the bottom insert from the detachable foot cavity when a set screw is inserted through the detachable foot to abut the side surface.

8. The apparatus of claim 6, further comprising a separating plate between the bottom insert and a locking insert, the separating plate extending laterally from the locking insert.

9. The apparatus of claim 1, wherein each leg of the plurality of legs is a straight leg.

10. The apparatus of claim 9, wherein the pylon is connected to the connector positioned between the pylon and the prosthetic limb socket.

11. The apparatus of claim 1, wherein each leg of the plurality of legs is coupled below the base plate.

12. The apparatus of claim 1, wherein at least one of the plurality of legs and the central leg terminates in a rubber foot shaped to fit over a distal portion of the at least one of the plurality of legs or the central leg.

13. The apparatus of claim 1, wherein the base plate is planar with four sides and comprises a lateral extension, the lateral extension comprising a distal end connected to at least one of the plurality of legs.

14. The apparatus of claim 1, wherein the pylon connects to the base plate at a connection point on the base plate and the connection point is off-center from a center of the base plate.

15. The apparatus of claim 1, wherein the locking element is a quick-release connector.

16. The apparatus of claim 1, wherein:
the base plate has at least two corners; and
the plurality of legs comprise at least two legs coupled below the at least two corners.

17. The apparatus of claim 1, wherein:
the base plate has at least four corners; and
the plurality of legs comprise at least four legs.

* * * * *